United States Patent [19]

Sickafus

[11] Patent Number: 4,974,552
[45] Date of Patent: Dec. 4, 1990

[54] ENGINE CONTROL SYSTEM RESPONSIVE TO OPTICAL FUEL COMPOSITION SENSOR

[75] Inventor: Edward N. Sickafus, Grosse Ile, Mich.

[73] Assignee: Ford Motor Company, Dearborn, Mich.

[21] Appl. No.: 462,187

[22] Filed: Jan. 9, 1990

[51] Int. Cl.$^5$ ............... F02M 43/00; G01N 21/00
[52] U.S. Cl. ................... 123/1 A; 73/61.1 R; 123/494; 123/575; 250/343; 250/574
[58] Field of Search ........... 123/1 A, 478, 494, 575; 73/61.1 R; 250/343, 574

[56] References Cited

U.S. PATENT DOCUMENTS

| | | | |
|---|---|---|---|
| 3,639,770 | 2/1972 | Zizelmann | 250/574 |
| 4,438,749 | 3/1984 | Schwippert | 123/494 |
| 4,594,968 | 6/1986 | Degobert et al. | 123/1 A |
| 4,706,630 | 11/1987 | Wineland et al. | 123/1 A X |
| 4,770,129 | 9/1988 | Miyata et al. | 123/1 A |

Primary Examiner—Tony M. Argenbright
Attorney, Agent, or Firm—Allan J. Lippa; Peter Abolins

[57] ABSTRACT

An engine control system for operating an internal combustion engine with any mixture of alcohol and gasoline. The control system includes an air/fuel ratio control system providing a desired fuel charge in relation to the alcohol and gasoline content of the fuel which is indicated by an optical sensor. In one embodiment, the optical sensor includes a hemispherical lens having hemispherical recesses formed through the lens base equidistant from the lens plane of symmetry. A light emitting diode positioned in one recess irradiates substantially the entire 2 $\pi$ steradian outer surface of the hemispherical lens. A portion of the transmitted light is reflected from substantially the entire hemispherical lens and substantially focused on a photodetector positioned in the other recess. Emitter and detector are substantially positioned at conjugate focii of the lens which provides substantially a 2 $\pi$ steradian collection aperture. The amount of transmitted light reflected is related to the index of refraction of the surrounding fuel mixture thereby providing a measurement of fuel composition.

19 Claims, 4 Drawing Sheets

ENGINE CONTROL SYSTEM RESPONSIVE TO OPTICAL FUEL COMPOSITION SENSOR

BACKGROUND OF THE INVENTION

The field of the invention relates to optical refractory sensors for determining the composition of a fluid medium. In one particular aspect of the field, the invention relates to engine air/fuel ratio control based on a determination of the composition of an alcohol/gasoline fuel mixture utilizing optical reflection detection.

Demand is increasing for motor vehicles which are operable with a mixture of alcohol, such as methanol or ethanol, and a hydrocarbon fuel such as gasoline or diesel oil. Since availability of both alcohol and gasoline will vary geographically and seasonally, vehicles are needed which may operate with any fuel mixture between 15% alcohol/85% gasoline and 100% gasoline. Further, the fuel blen may vary between refueling events such that the exact blend in a fuel tank may never be known by the operator. One problem with such vehicles is that alcohol has approximately one-half the energy density of gasoline. Thus, to maintain adequate power and drivability, the fuel delivered for each combustion event must increase in relation to the alcohol content of the fuel mixture. Other engine operating parameters such as ignition timing may also be altered as a function of alcohol content. Accordingly, a need exist for highly accurate sensors to detect the constituent composition of an alcohol/gasoline fuel mixture.

Typical optical sensors which determine the amount of alcohol and gasoline combined in a fuel mixture are disclosed in U.S. Pat. No. 4,438,749 issued to Schwippert and U.S. Pat. No. 4,770,129 issued to Miyata et al. These sensors are referred to as critical angle sensors, a representative embodiment of which is illustrated herein by FIG. 1 which is labeled Prior Art. The sensor shown includes a glass column or bar having a bottom surface immersed in the fuel mixture. A light emitting diode (LED) and a photodetector are glued to opposing ends of the glass bar. For a fuel composed of 100% gasoline, a light beam (labeled as pure gasoline) is shown striking and reflected from the glass/fuel boundary (point "g") at critical angle $\theta_g{}^c$. The critical angle is determined by the trigonometric relationship sine $\theta_a{}^c =$ ratio of refractive indices for gasoline and glass. Assuming a pure gasoline mixture, all light striking the boundary at an angle greater than $\theta_g{}^c$ will be reflected. Only a portion of light striking the boundary at less than $\theta_g{}^c$ will be reflected, the remaining portion being refracted. Similarly, for a fluid mixture of 100% alcohol, a light beam (labeled pure ethanol) is shown striking the boundary (point "a") at critical angle $\theta_a{}^c$ and reflected therefrom. Assuming a fuel mixture of pure alcohol, all light striking the boundary at an angle greater than $\theta_a{}^c$ will be reflected, while only a portion of light at less than $\theta_a{}^c$ will be reflected. The photodetector is positioned such that only light striking the glass/fuel mixture boundary between points "a" and "g" is reflected onto the photodetector. Thus, an effective collection aperture of the sensor is defined by the distance between points "a" and "g" on the boundary surface.

The critical angle for a particular fuel mixture is a function of the average composition by molecular fraction of alcohol and gasoline and their respective indicies of refraction as determined by the well known Lorentz-Loreng formula. For example, the critical angle for a hypothetical fluid mixture of 50% alcohol and 50% gasoline is shown by $\theta_m{}^c$ at boundary point "m". With this hypothetical mixture, light striking the boundary between points "m" and "g" is totally reflected to the detector. Light striking the boundary between points "m" and "a" is partially refracted into the fluid mixture and partially reflected to the detector. The unique amount of light reflected onto the photodetector is directly related to the amount of alcohol in the fluid mixture. This relationship can be derived from the Lorentz-Lorenz formula or other similar expressions. Thus, from the electrical signal generated by the photodector, the volume composition of alcohol and gasoline can be identified.

The critical angle approach using a planar interface boundary as described above has numerous disadvantages. One disadvantage is that the effective collection aperture (between points "a" and "g") on the glass/fluid boundary is relatively small resulting in a poor detected signal-to-noise ratio. Another disadvantage is that a portion of emitted light from the LED directly irradiates the detector. Compensation must be provided for this directly transmitted light or it must be blocked thereby adding complexity to the sensor. Still another disadvantage is caused by the gap between the LED and glass bar, and the gap between the detector and glass bar. These gaps are typically filed with and epoxy having a different index of refraction than glass. Accordingly, portions of light emitted by the LED are both reflected and refracted at the gap/glass boundary. A similar phenomenon occurs with reflected light at the glass/gap boundary before the detector. These factors further reduce the signal-to-noise ratio of the sensor.

SUMMARY OF THE INVENTION

An object of the invention herein is to provide an optical sensor with a greater effective collection aperture, and higher overall detected signal to noise ratio then heretofore possible.

The disadvantages of prior approaches are overcome, and object achieved, by an optical sensor for determining the ratio of each of two constituents in a fluid mixture wherein each constituent has a different index of refraction. In one particular aspect of the invention, the optical sensor comprises: a hemispherical lens having an axis, a hemispherical surface surrounded by the fluid mixture, and a substantially flat base; a light emitting source aligned with the axis and positioned adjacent to the base for transmitting light against substantially all of the hemispherical surface; and a light detector aligned with the axis and positioned adjacent to the base and the light emitting source, the light detector collecting light which is reflected from substantially all of the hemispherical surface such that the optical sensor has an effective aperture of nearly $2\pi$ steradians, the light detector providing an electrical signal related to the proportion of the constituents in the fluid mixture.

An advantage of the above aspect of the invention is that the sensor has an effective collection aperture of nearly $2\pi$ steradians which is substantially greater than heretofore possible. Another advantage is gained by axially placing the light detector around the light emitter. More specifically, the light emitter radiates light above the detector thereby eliminating direct transmission of light to the detector which was a disadvantage of prior approaches.

In another aspect of the invention, the optical sensor comprises: a hemispherical lens having an axis, a hemispherical surface surrounded by the fluid mixture, and a substantially flat base with an axially aligned recess formed in the base; a light emitting source positioned in the recess which irradiates substantially all of the hemispherical surface; and a light detector positioned adjacent the base below the light emitting source and aligned with the axis, the light detector collecting light which is transmitted from the light source and reflected from substantially all of the hemispherical surface such that the optical sensor has an effective collection aperture of nearly $2\pi$ steradians, the light detector providing an electrical signal related to the proportion of constituents in the fluid mixture. Preferably, the recess in the bottom surface includes a hemispherical portion wherein the light source irradiates the hemispherical portion such that substantially all of the transmitted light is transmitted with minimal reflection through the hemispherical portion.

An advantage of the above aspect of the invention is that the sensor has an effective collection aperture of nearly $2\pi$ steradians which is substantially greater than heretofore possible. Another advantage is gained by placing the detector below the light emitter. More specifically, the light emitter radiates light above the detector thereby eliminating direct transmission of light to the detector which was a disadvantage of prior approaches. Still another advantage is gained by placing the emitter within a recess having a hemispherical portion. By such an arrangement, emitted light perpendicularly impinges upon the hemispherical portion. Reflected and refracted light at the emitter/lens boundary is thereby substantially eliminated resulting in a higher signal to noise ratio than heretofore possible.

In another aspect of the invention, the optical sensor comprises: a hemispherical lens having its hemispherical surface surrounded by the fluid mixture and also having a substantially flat base, the hemispherical lens having a plane of symmetry symmetrical about a center axis of the hemispherical lens; a light emitting source positioned in a recess within the base which is offset a predetermined distance from the plane of symmetry, the light source irradiating substantially all of the hemispherical surface; and a light detector positioned substantially at a conjugate focii to the light emitting source which is opposite the plane of symmetry with respect to the light emitting source by a distance substantially equal to the predetermined distance, the light detector collecting light which is transmitted from the light source and reflected from substantially all of the hemispherical surface such that the optical sensor has an effective collection aperture of nearly $2\pi$ steradians, the light detector providing an electrical indication of the constituents in the fluid mixture. Preferably, the light detector is located on an opposite side of the plane of symmetry with respect to the light emitting source and below the light emitting source.

An advantage of the above aspect of the invention is that the sensor has an effective collection aperture of nearly $2\pi$ steradians which is substantially greater than heretofore possible. Another advantage is gained by positioning the light detector at a conjugate focii to the emitter. More specifically, reflective light is concentrated at the conjugate focii enabling a much smaller detector and a higher signal noise ratio. Still another advantage is gained by placing the detector below the emitter. More specifically, the light emitter only radiates light above the detector thereby eliminating direct transmission of the light to the detector and further enhancing the detected signal to noise ratio.

DESCRIPTION OF THE PREFERRED EMBODIMENT

Figure 2:
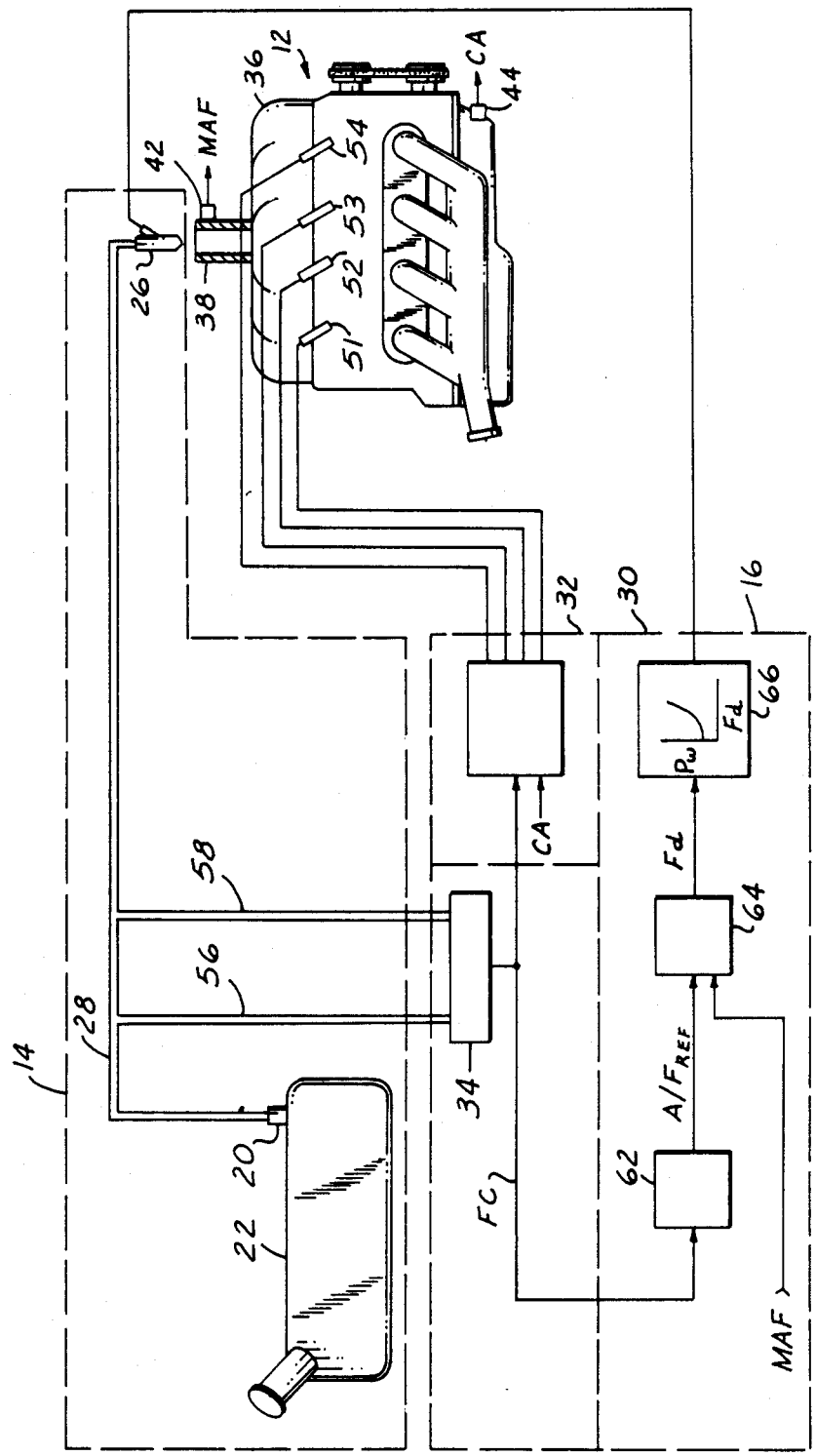
FIG. 2 shows the engine, fuel system and engine control system.

Referring first to FIG. 2, internal combustion engine 12 is shown receiving fuel from fuel system 14 and controlled by engine control system 16. Fuel system 14 is shown including fuel pump 20 coupled to fuel tank 22 for delivering fuel to conventional fuel injector 26 via fuel line 28. Conventional fuel rails, pressure regulators, and fuel return lines are not shown because they are not necessary for an understanding of the invention. As described in greater detail later herein, engine control system 16 controls engine operating parameters such as air/fuel ratio and ignition timing so that engine 12 may operate with different fuel mixtures. For the example described herein, a fuel mixture is composed of a combination of alcohol, such as ethanol or methanol, and gasoline. Engine control system 16 is shown including air/fuel ratio control system 30, ignition controller 32, and fuel composition sensor 34.

Engine 12 is shown including intake manifold 36 coupled to air/fuel intake 38 for inducting a mixture of air and fuel into each combustion chamber (not shown). Air/fuel intake 38 is shown receiving fuel from fuel injector 26 which in turn is controlled by air/fuel ratio control system 30 of engine control system 16. Air/fuel ratio control system 30 receives a measurement of inducted mass airflow (MAF) from mass airflow sensor 42 which is coupled to air/fuel intake 38. Engine control system 16 is also shown including ignition controller 32 which provides ignition timing to spark plugs 51, 52, 53 and 54 as a function of engine crankshaft position. Conventional crank angle sensor 44 is coupled to the engine crankshaft (not shown) for providing ignition controller 32 with a crank angle position signal (CA).

Figure 1:
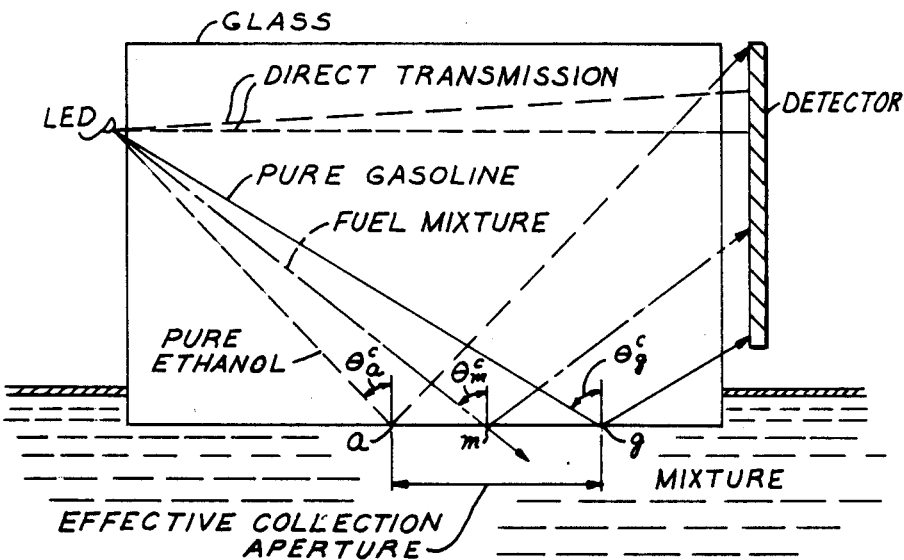
FIG. 1 shows a representative embodiment of a prior art critical angle fuel composition sensor.
Figure 3:
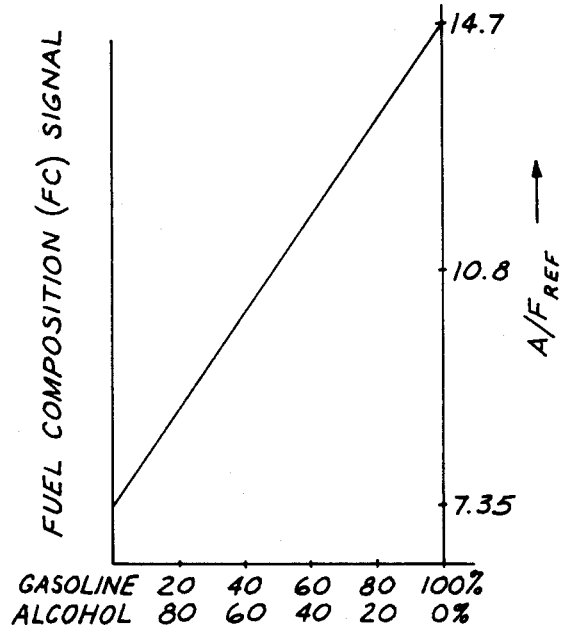
FIG. 3 shows the output of the fuel composition sensor relative to the volume percentage of alcohol and gasoline in the fuel mixture.
Figure 4C:
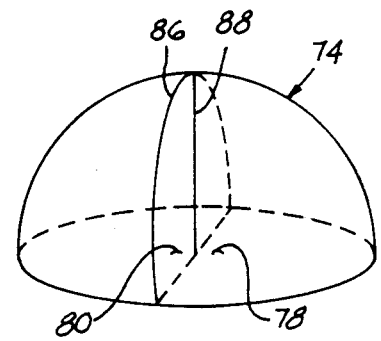
FIGS. 4A, 4B and 4C show details of a first embodiment of the fuel composition sensor.

As described in greater detail later herein, fuel composition sensor 34 of engine control system 16 is coupled to fuel line 28 via inlet line 56 on return line 58. Referring to FIG. 3, and continuing with FIG. 2, fuel composition sensor 34 provides fuel composition signal FC, having an amplitude related to the volume percentage of alcohol and gasoline in the fuel mixture. Fuel composition signal FC is provided to both air/fuel ratio control system 30 and ignition control system 32.

Air/fuel ratio control system 30 includes $A/F_{Ref}$ generator 62, desired fuel charge calculator 64, and pulse width convertor 66. In response to fuel composition signal FC $A/F_{Ref}$ generator 62 converts the volume representation of fuel composition to a mass representation by a density algorithm and provides air/fuel reference signal $A/F_{Ref}$ as a function of the density of alcohol and gasoline composition. Since alcohol has one atom of oxygen per molecule, $A/F_{Ref}$ will decrease with increasing alcohol content. Stated another way, a greater mass of fuel is required per pound of air with increasing alcohol concentration.

Fuel charge calculator 64 then divides signal $A/F_{Ref}$ by signal MAF to obtain desired fuel charge signal Fd. In response to desired fuel charge signal Fd, pulse width convertor 66 (such as a lookup table) provides signal pw, having a pulse width related to desired fuel charge, to injector 26. Accordingly, the air/fuel mixture inducted by engine 12 will maintain a desired air/fuel ratio as determined by the composition of the alcohol/gasoline mixture.

Those skilled in the art will recognize that although an open loop air/fuel ratio control system was shown, the invention described herein is applicable to feedback air/fuel ratio control systems responsive to an exhaust gas oxygen sensor. Further, the invention is also applicable to multi port fuel injected systems and carbureted fuel injected systems.

Continuing with FIG. 2, ignition controller 32 is shown responsive to fuel composition signal FC and crank angle signal CA. During operation with pure gasoline, ignition energy is supplied to the appropriate combustion chamber (not shown) during its compression stroke a predetermined number of crank angle degrees before top-dead-center position of the cylinder (typically 20°). With increasing alcohol composition in the fuel mixture, however, ignition controller 32 appropriately advances the ignition timing to provide longer burn duration. It is noted that other engine operating parameters, such as exhaust gas recirculation (EGR), and cold start enrichment may also be adjusted as a function of fuel mixture but have not been described herein.

Figure 4A:
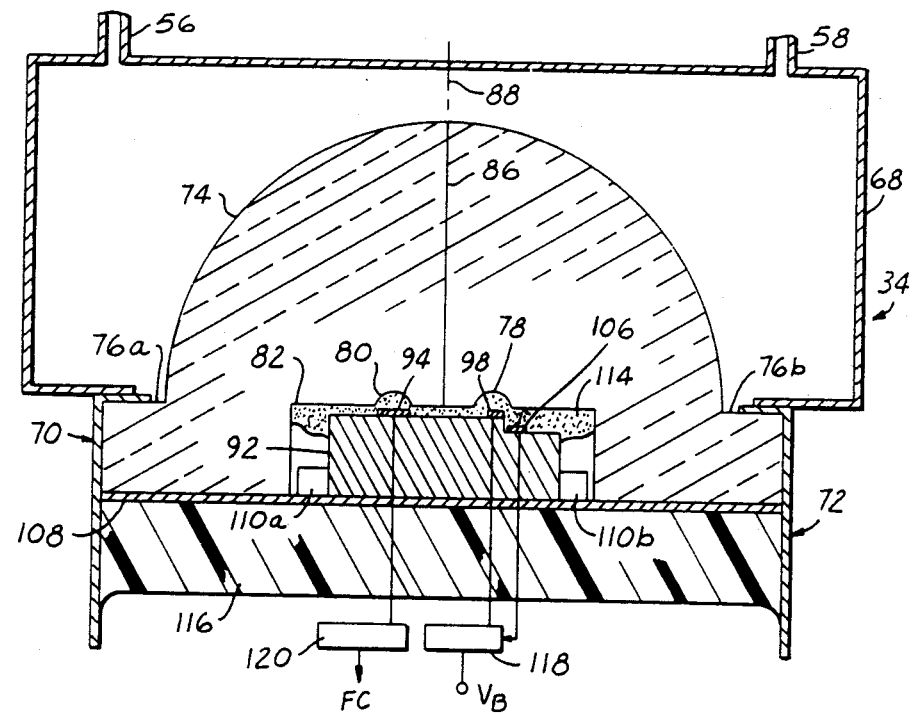

Referring now to FIG. 4A, fuel composition sensor 34 is shown including fuel reservoir 68 having optical sensor assembly 70 inserted therein and communicating with fuel system 14. Fuel reservoir 68 is coated internally with a nonreflective material for reasons which will become apparent later herein. Optical sensor assembly 70 includes hemispherical lens 74 which is constructed of glass in this example although other materials such as a coated plastic resin or a resin/glass composition may be used to advantage. Hemispherical lens 74 is shown including shoulders 76a and 76b for mounting with canister 72. As described in greater detail later herein, hemispherical recess 78 and hemispherical recess 80 are formed through base 82 of lens 74 an equal distance apart from lens plane of symmetry 86 which passes through lens axis 88.

Substrate 92 is shown positioned below base 82 for mounting photodetector 94, a phototransistor, and light emitter 98, a light emitting diode, thereon. Emitter 98 is slightly elevated from detector 106 for reasons described later herein. Substrate 92 includes recess 102 having monitor 106, another conventional photodetector, mounted thereon. Substrate 92 is shown positioned on canister divider 108 between alignment tabs 110a and 110b. Epoxy layer 114, chosen with an index of refraction close to glass, is shown covering emitter 98, photodetector 94, and monitor 106. Potting compound layer 116 is shown covering the bottom surface of divider 108 and the electrical lead wire pairs to photodetector 94, emitter 98, and monitor 106.

Regulated voltage supply 118 regulates electrical energy supplied to emitter 98 in response to a feedback signal from light monitor 106. Emitter 98 transmits light in relation to electrical energy supplied thereto. A portion of this emitted light is reflected from hemispherical lens 74 onto monitor 106. Regulated voltage supply 118 maintains the light output from emitter 98 at a substantially constant value in response to feedback from light monitor 106 thereby compensating for the effect of emitter aging.

Circuitry 120, preferably an analog amplifier, buffers the output of detector 94 to provide fuel composition signal FC to engine control system 16. In some applications, such as when microprocessors are used in the engine controller, circuitry 120 includes an analog to digital convertor.

The operation of optical sensor assembly 74 is described in more detail with reference to FIG. 4B. A cross-sectional view of hemispherical lens 74 is shown having a number of transmitted, reflected, and refracted light beams illustrated. Emitter 98 irradiates substantially the entire $2\pi$ steradian surface of hemispherical lens 74 although only a few light beams are shown for illustrative purposes. An unusual and novel phenomenon is noted wherein substantially all reflected light is focused at a conjugal focal point 122. More specifically, conjugal focal point 122 is formed distance "d" from plane of symmetry 86 which is substantially the same distance "d" that focal point 124 of emitter 98 is positioned from plane of symmetry 86. Focal point 122 is also formed slightly below focal point 124. Accordingly, substantially all transmitted light which is reflected from the outer surface of hemispherical lens 74 is focused at focal point 122 and collected by photodetector 94. A smaller photodetector operating with a higher signal to noise ratio than heretofore possible is therefore utilized. Further, as previously stated herein, the effective collection aperture of hemispherical lens 74 is substantially $2\pi$ steradians which is far greater than heretofore possible.

Transmitted light is both reflected from, and refracted through, the entire $2\pi$ steradian surface of hemispherical lens 74. A portion of each transmitted light beam is reflected, the specific amount reflected being a function of its angle of incidence and the ratio of refractive indices between the glass lens and surrounding fuel mixture as determined by the following equation:

$$R = \left( \frac{\tan \theta_i - \tan \theta_t}{\tan \theta_i + \tan \theta_t} \right)^2$$

where $$\theta_t = \operatorname{Sin}^{-1} \left( \frac{N_{glass}}{N_{fuel}} \operatorname{Sin} \theta_i \right)$$

and $\theta_i$ is the angle of incidence on the hemisphere.

Since alcohol has a lower refractive index than gasoline, the amount of transmitted light reflected increases with increasing alcohol content in the fuel mixture. Thus, the electrical output of photodetector 94 (signal FC) is directly related to the ratio of alcohol/gasoline in the fuel mixture. Stated another way, the greater the percentage of alcohol as a constituent of the alcohol/gasoline fuel mixture, the larger is fuel composition signal FC.

Figure 4B:
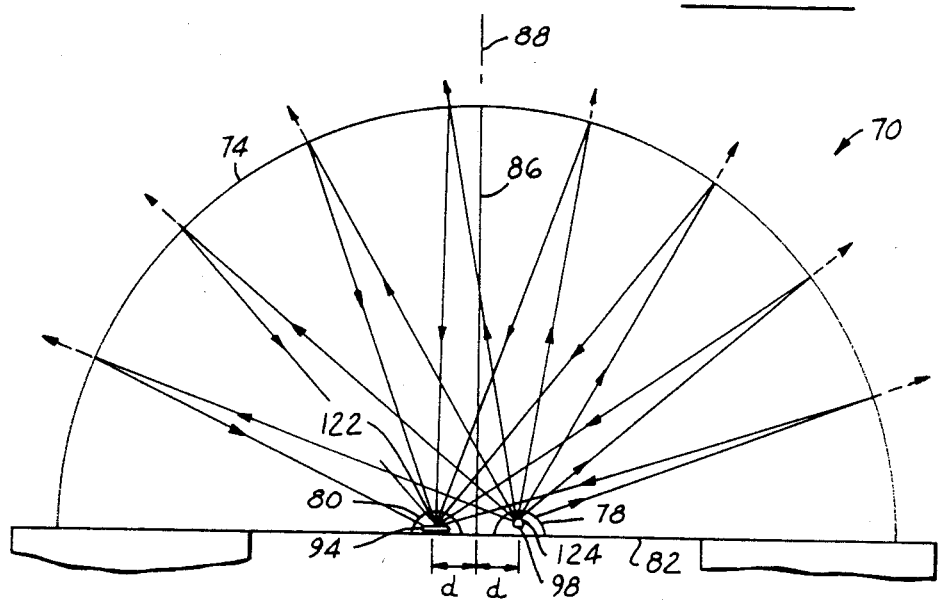

FIG. 4B illustrates that the angles of incidence for a light beam incident on the outer surface of lens 74 is negatively related to the angle of emission with respect to axis 88. Thus, the portion of light reflected from the lens surface is greater near axis 88 than it is near base 82. Accordingly, offsetting emitter 98 from plane of symmetry 86, or lens axis 88, increases the average signal strength of reflected light.

It is further noted that by positioning emitter 98 within hemispherical recess 78, emitted light strikes hemispherical lens 74 at an angle of incidence of substantially 90°. Thus, reflection of light upon entering lens 74 is minimized and transmission maximized thereby overcoming a disadvantage of prior approaches. Similarly, photodetector 94 is positioned within hemispherical recess 80 such that substantially all light relrected from hemispherical surface 74 will arrive at near normal incidence on recess 80 with a subsequent maximization of the signal at detector 94.

Figure 5:
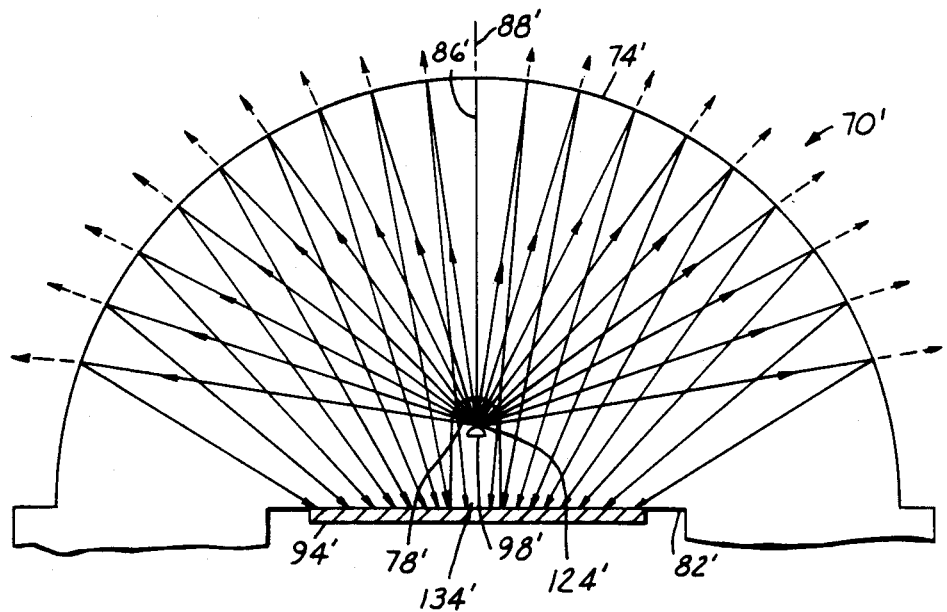
FIGS. 5 and 6 show two alternate embodiments of the fuel composition sensor.

An alternate embodiment of the optical sensor assembly is shown in FIG. 5 wherein like numerals refer to like parts shown in the embodiment presented in FIGS. 4A, and 4B. In this embodiment, recess 134' is shown axially formed through base 82' and is also shown having hemispherical end 78'. Emitter 98' is positioned within recess 134' such that transmitted light enters hemispherical lens 74' at a 90° angle to the lens/recess boundary at hemispherical end 78' thereby substantially minimizing light scattering upon entering hemispherical lens 74'. Transmitted light is shown both reflected from and refracted through the entire 2 $\pi$ steradian surface of hemispherical lens 74'. A portion of each transmitted light beam is reflected and the specific amount reflected is a function of its angle of incidence and the ratio of refractive indices between glass and the fuel mixture as described previously herein. FIG. 5 illustrates that the angle of incidence for a light beam incident on the outer surface of lens 74' is greater, the greater is the angle of emission with respect to axis 88'. Therefore, the proportion of light reflected from the surface of hemispherical lens 74' increases with movement from axis 88' to base 82'.

Photodetector 94' is shown positioned on base 82' for collecting substantially all light reflected from the outer surface of hemispherical lens 74'. Photodetector 94' is shown positioned below emitter 98' such that direct transmission of light from emitter to photodetector is eliminated which was a problem of prior approaches. As described previously herein, photodetector 94' provides an electrical output (fuel composition signal FC) which is directly related to the amount of light reflected and, accordingly, the alcohol/gasoline ratio of the fuel mixture.

Figure 6:
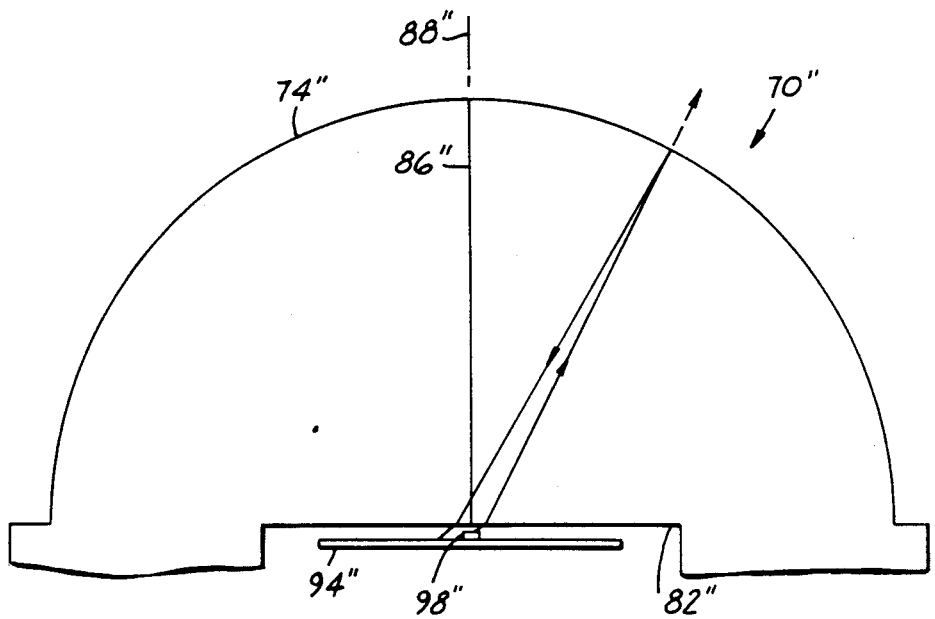

Another alternate embodiment is shown in FIG. 6 wherein in like numerals refer to like parts shown in the embodiment represented by FIGS. 4A and 4B, and the alternate embodiment represented by FIG. 5. In this particular embodiment, emitter 98" is shown positioned below base 82" and axially aligned with lens axis 88". Stated another way, emitter 98" is aligned with plane of symmetry 86". Since emitter 98" is aligned with lens axis 88"', and near base 82"', light strikes the outer surface of hemispherical lens 74" at an angle of incidence which is an average less than the angle of incidence associated with the embodiments described previously herein. Accordingly, the total of reflected light is less than the other embodiments shown herein. However, as was the case with the other embodiments, light is reflected from the entire 2 $\pi$ steradian outer surface of lens 74" thereby resulting in an effective collection aperture of essentially 2 $\pi$ steradians which is greater than heretofore possible. Further, photodetector 94" is either positioned below emitter 98" (as shown in FIG. 6) or, alternatively, emitter 98" is recessed within the center portion of photodetector 94". In either case, direct transmission of light from emitter 98" to photodetector 94" is substantially eliminated thereby providing a detection advantage.

This concludes the description of the preferred embodiment. The reading of it by those skilled in the art will bring to mind many alterations and modifications without departing from the spirit and scope of the invention. For example, the invention described herein may be used to provide the constituent composition of other fuel mixtures besides an alcohol/gasoline fuel mixture, and it may be used to differentiate alcohol-free gasoline blends. Further, the invention may be used to advantage to discriminate the constituent composition of fuel fluids other than fuel mixtures. In addition, the invention described herein is not limited to use in internal combustion engine control systems. Accordingly, it is intended that the scope of the invention be limited only by the following claims.

What is claimed:

1. An optical sensor for determining the ratio for each of two constituents in a fluid mixture wherein each constituent has a different index of refraction, comprising:

a hemispherical lens portion having an axis, a hemispherical surface surrounded by the fluid mixture, and a base;

a light emitting source aligned with said axis and positioned adjacent to said base for transmitting light against substantially all of said hemispherical surface; and a light detector aligned with said axis and positioned on said base adjacent said light emitting source, said light detector collecting light which is reflected from substantially all of said hemispherical surface such that the optical sensor has an effective aperture of nearly 2 $\pi$ steradians, said light detector providing an electrical signal related to the proportion of the constituents in the fluid mixture.

2. The optical sensor recited in claim 1 wherein a ratio of said reflected light to said transmitted light is related to a ratio of refractive indices of the mixture constituents.

3. The optical sensor recited in claim 1 wherein the mixture constituents comprise alcohol and gasoline.

4. The optical sensor recited in claim 1 wherein said light emitting source comprises a light emitting diode.

5. The optical sensor recited in claim 1 wherein said light detector comprises a photodetector and said light emitting source comprises a light emitting diode, the optical sensor further comprising feedback means responsive to light reflected by said hemispherical lens for regulating electrical power supplied to said light emitting diode such that its emitted light remains substantially constant.

6. An optical sensor for determining the proportion of each of two constituents in a fluid mixture wherein each constituent has a different index of refraction, comprising:

a hemispherical lens portion having an axis, a hemispherical surface surrounded by the fluid mixture, and a base with an axially aligned recess formed in said base;

a light emitting source positioned in said recess which irradiates substantially all of said hemispherical surface; and a light detector positioned adjacent said base directly below said light emitting source and aligned with said axis, said light detector collecting light which is emitted from said light source and reflected from substantially all of said hemispherical surface such that the optical sensor has an effective aperture of nearly $2\pi$ steradians, said light detector providing an electrical signal related to the proportion of constituents in the fluid mixture.

7. The optical sensor recited in claim 6 wherein said recess in said bottom surface includes a hemispherical portion and wherein said light source irradiates said hemispherical portion such that substantially all of said emitted light is transmitted through said hemispherical portion.

8. The optical sensor recited in claim 6 wherein a ratio of said reflected light to said emitted light is related to a ratio of refractive indices of the mixture constituents.

9. The optical lens recited in claim 6 wherein the mixture constituents comprise alcohol and gasoline.

10. An optical sensor for determining constituents of a fluid mixture wherein each constituent has a different index of refraction, comprising:

a hemispherical lens having its hemispherical surface surrounded by said fluid mixture and also having a base, said hemispherical lens having a plane of symmetry symmetrical about a center axis of said hemispherical lens;

a light emitting source positioned in a recess within said base which is offset a predetermined distance from said plane of symmetry, said light source irradiating substantially all of said hemispherical surface; and a light detector positioned substantially at a conjugate focus to said light emitting source which is opposite said plane of symmetry with respect to said light emitting source by a distance substantially equal to said predetermined distance, said light detector collecting light which is transmitted from said light source and reflected from substantially all of said hemispherical surface such that the optical sensor has an effective aperture of nearly $2\pi$ steradians, said light detector providing an electrical indication of the constituents in the fluid mixture.

11. The optical lens recited in claim 10 wherein said recess in said bottom surface includes a hemispherical portion and wherein said light source irradiates said hemispherical portion such that substantially all of said transmitted light is transmitted through said hemispherical portion.

12. The optical lens recited in claim 10 wherein said conjugate focal point is located on an opposite side of said plane of symmetry with respect to said light emitting source and below said light emitting source.

13. The optical lens recited in claim 10 wherein said light detector is positioned on said base.

14. The optical lens recited in claim 10 wherein a ratio of said reflected light to said transmitted light is related to a ratio of refractive indices of the mixture constituents.

15. A control system for an internal combustion engine which operates with a fuel mixture composed substantially of two constituents each having a different index of refraction, said control system comprising:

a hemispherical lens having an axis, a hemispherical surface surrounded by the fluid mixture, and a base with an axially aligned recess formed in said base;

a light emitting source positioned in said recess which irradiates substantially all of said hemispherical surface;

a light detector positioned adjacent said base directly below said light emitting source and aligned with said axis, said light detector collecting light which is transmitted from said light source and reflected from substantially all of said hemispherical surface such that the optical sensor has an effective aperture of nearly $2\pi$ steradians; and control means responsive to said light detector for adjusting an engine operating parameter as a function of constituent composition of the fuel mixture.

16. The control system recited in claim 15 wherein said control means regulates engine air/fuel ratio in relation to the constituent composition of the fuel mixture.

17. The control system recited in claim 15 wherein said control means regulates engine ignition timing in relation to the constituent composition of the fuel mixture.

18. A control system for an internal combustion engine which inducts a mixture of air and a fuel mixture composed of two constituents wherein each constituent has a different index of refraction, said control system comprising:

a hemispherical lens having its hemispherical surface surrounded by said fluid mixture and also having a base, said hemispherical lens having a plane of symmetry symmetrical about a center axis of said hemispherical lens;

a light emitting source positioned in a recess within said base which is offset a predetermined distance from said plane of symmetry, said light source irradiating substantially all of said hemispherical surface;

a light detector positioned substantially at a conjugate focal point to said light emitting source which is opposite said plane of symmetry with respect to said light emitting source by a distance substantially equal to said predetermined distance, said light detector collecting light which is transmitted from said light source and reflected from substantially all of said hemispherical surface such that the optical sensor has an effective aperture of nearly $2\pi$ steradians, said light detector providing an indication of the constituents in the fluid mixture;

reference means responsive to said light detector for providing an air/fuel ratio reference as a function of constituent composition of the fuel mixture;

airflow means for calculating airflow inducted into the engine; and air/fuel ratio means for delivering fuel into the engine in response to said inducted airflow calculation and said air/fuel ratio reference such that the engine operates at said air/fuel ratio reference.

19. The optical sensor recited in claim 18 wherein said light detector comprises a photodetector and said light emitting source comprises a light emitting diode, said optical sensor further comprising feedback means responsive to light reflected by said hemispherical lens for regulating electrical power supplied to said light emitting diode such that its emitted light remains substantially constant.

* * * * *